United States Patent [19]

Nakao et al.

[11] Patent Number: 4,790,528
[45] Date of Patent: Dec. 13, 1988

[54] TRAINING DEVICE FOR REHABILITATION

[75] Inventors: Shinroku Nakao, Kanagawa; Masao Ito, Tokyo, both of Japan

[73] Assignee: Combi Co., Ltd., Tokyo, Japan

[21] Appl. No.: 32,647

[22] Filed: Mar. 31, 1987

[30] Foreign Application Priority Data

Jul. 29, 1986 [JP] Japan .................................. 61-178470

[51] Int. Cl.$^4$ ............................................. A63B 69/16
[52] U.S. Cl. ............................... 272/73; 272/DIG. 6; 128/25 R
[58] Field of Search ........................... 272/73, DIG. 6; 128/25 R

[56] References Cited

U.S. PATENT DOCUMENTS 4,378,111 3/1983 Tsuchida et al.
4,678,182 7/1987 Nakao et al. ............................ 272/73

FOREIGN PATENT DOCUMENTS 0131088 of 0000 European Pat. Off.
3404539 8/1985 Fed. Rep. of Germany.
3428675 2/1986 Fed. Rep. of Germany.
81/01507 11/1981 PCT Int'l Appl.

OTHER PUBLICATIONS

European Search Report dated 10/11/87.

Primary Examiner—Leo P. Picard
Attorney, Agent, or Firm—Sughrue, Mion, Zinn, Macpeak, and Seas

[57] ABSTRACT

A rehabilitation training device and method in which a target heart rate is input, the heart rate is measured and a load in an ergometer operated by the person undergoing rehabilitation is changed accordingly. There are four steps in the training: (1) warm up—the load is increased to have the heart rate linearly approach the target value; (2) automatic—the load is varied to maintain the heart rate at the target; (3) interval—the load is alternated between its average value in the automatic step and a fraction thereof, and (4) cool-down-the load is gradually decreased.

4 Claims, 6 Drawing Sheets

TRAINING DEVICE FOR REHABILITATION

BACKGROUND OF THE INVENTION

1. Field of the Invention

This invention relates to a training device for rehabilitation which can be readily used for rehabilitation of a person at his home who has recovered, for instance, from heart disease. In such a training device, the load is controlled by heart rate measuring means, which is based on electro-cardio-potential, in order to maintain a relatively low target heart rate. The load is further controlled suitably in the warming-up stage and in the interval training stage according to the strength of the legs or waist of the person who has recovered from the illness by surgical operation, thereby to increase his physical strength.

2. Background of the Invention

A variety of so-called "bicycle ergometer type training devices" are commercially available in which, in response to instructions from a microcomputer built therein, the physical conditions of a person (age, weight, sex and heart rate) are inputted. There data are processed so that an optimum load value and a controlled heart rate under the load are determined. The exercise of the person (user or operator) is continuously controlled according to these data. Reference is made to Japanese Patent Applications No. 123172/1983 entitled "Method of Determining the Best Exercise Conditions", No. 123173/1983 entitled "Training Device", and No. 69922/1984 entitled "Training Device" which have been filed by the present applicant.

Of these conventional training devices, one is generally provided for a healthy person in which the load is automatically controlled so as to maintain the heart rate at a predetermined target value and therefore its target heart rate is high. Therefore, the training device is not suitable for a person who is being rehabilitated to restore the muscles of the legs and waist which been weakened by his being confined to bed with a disease. That is, with the training device, the warming up for allowing the heart rate to reach the target heart rate is considerably strenuous and abrupt for such a person. In addition, even after the heart rate has reached the target value, the load is increased. Thus, the conventional training device is unsuitable for those who need to be rehabilitated.

In almost all the conventional bicycle ergometers for healthy persons, the target heart rate is automatically set according to the statistical central values of past data which have been obtained separately according to ages and sexes. However, no such past data have been provided for those who have recovered from heart disease and are to be rehabilitated. Accordingly, depending on the conventional training device in which such past data are automatically set, it is impossible to apply even one of the target numbers of heart rates to these person. That is, the target numbers of heart rates for these persons depend greatly on their recovery conditions or physical strengths. Accordingly, the target numbers of heart rate and the rehabilitation training frequencies for them should be specified by their personal physicians and input data such as a target heart rate for the rehabilitation training should be manually inputted. However, in the above-described training device for healthy people, various data are automatically inputted and these input data are those which have been statistically determined from the past data. Therefore, in the conventional training device, it is impossible to input the data which are exactly applicable to those people. That is, it is impossible to correctly rehabilitate them with the conventional training device.

In the case of rehabilitation of a person who has recovered from heart disease, especially in the case of rehabilitation with a training device, the training itself would be dangerous for the person if it were carried out without correctly knowing the variations of his physical conditions which may occur during the training in addition to the physical conditions. There are a few facilities which can conduct the rehabilitation by correctly detecting the variations of physical conditions of a person which may occur during the exercise. Examples of such facilities are hospitals and rehabilitation centers where doctors are controlling the training. However, only a limited number of persons can utilize such excellent facilities.

For instance in America where the rehabilitation is conducted under such desirable conditions while being controlled by doctors, almost all the training devices are those which are designed for a healthy person. Accordingly, those training devices which are utilized with training programs for healthy people, are converted into ones for rehabilitation.

In the rehabilitation which is conducted with such a training device for those who have recovered from heart disease, the rehabilitation program is obtained merely by rearranging the training program provided for healthy people. For instance, in the case of the bicycle ergometer type training device, a target heart rate is determined in advance and the ergometer load increasing rate is so arranged that the heart rate of a rehabilitating person being trained reaches the target heart rate more slowly than those of a healthy person. Therefore, the training program thus rearranged may be useful for the rehabilitation training in which the heart rate of a person being trained reaches the target value only slowly. On the other hand, the fatigue of the muscles of the legs and the waist depends greatly on the physical strengths of persons to be rehabilitated. For instance, even though the heart rate is increasing slowly according to the aforementioned load increasing rate, i.e., it is ideally reaching the target value, sometimes the fatigue of the muscles of the legs and the waist increases so much that the training cannot be satisfactorily continued.

However, the inventors believe that it is no exaggeration to say that the training device for rehabilitation of a person who has recovered from heart disease in which the above-described difficulties have been eliminated has never been proposed in the art. There has been a strong demand for the quick development of a training device used only for rehabilitation of such persons.

SUMMARY OF THE INVENTION

In view of the foregoing, an object of this invention is to provide a training device for rehabilitation.

In the training device of the invention, at least four training steps, warming-up, automatic control, interval and cool-down, are provided. Physical data of a person to be rehabilitated who is at rest before the warming-up step and those which are measured several times during the warming-up step are processed by a predetermined processing means so that a load control setting range is determined for each of the training steps. According to the variation of the physical data of the person measured during continuous training, the load is increased or decreased so that the physical conditions conform to the load control setting ranges. In this training device, after the person is held at rest, a relatively long warming-up period is provided so that the heart rate of the person is increased substantially linearly towards the target value during the warming-up period. In the automatic control step, the heart rate set for the rehabilitation of the person is maintained substantially constant, and the average load value required for maintaining that heart rate is measured. The average load value is utilized in the following interval steps so that, while the target heart rate is maintained at an optimum value, the load is intermittently decreased thereby to reduce the load applied to the legs and the waist. Thereby the physical strength of the person who has recovered from the heart disease can be suitably increased.

DETAILED DESCRIPTION OF THE PREFERRED EMBODIMENTS

One example of a training device for rehabilitation according to this invention will be described with reference to the accompanying drawings.

Figure 1:
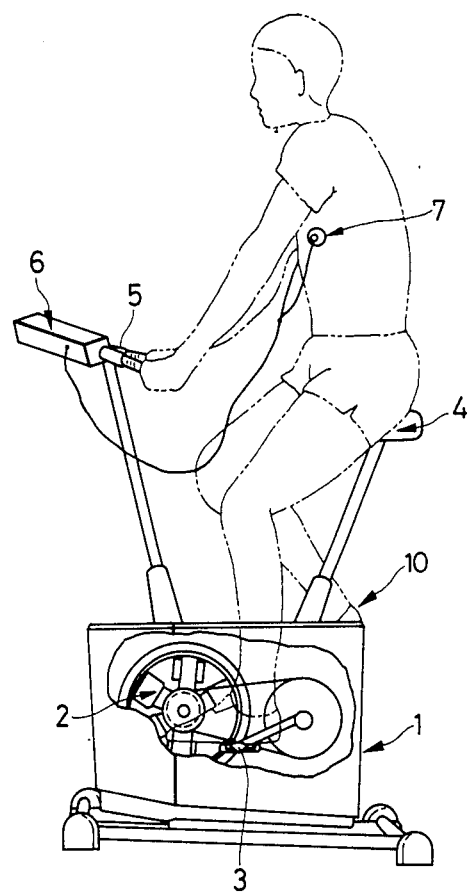
FIG. 1 is an explanatory diagram showing one example of a training device for rehabilitation according to this invention and the use thereof.
Figure 2:
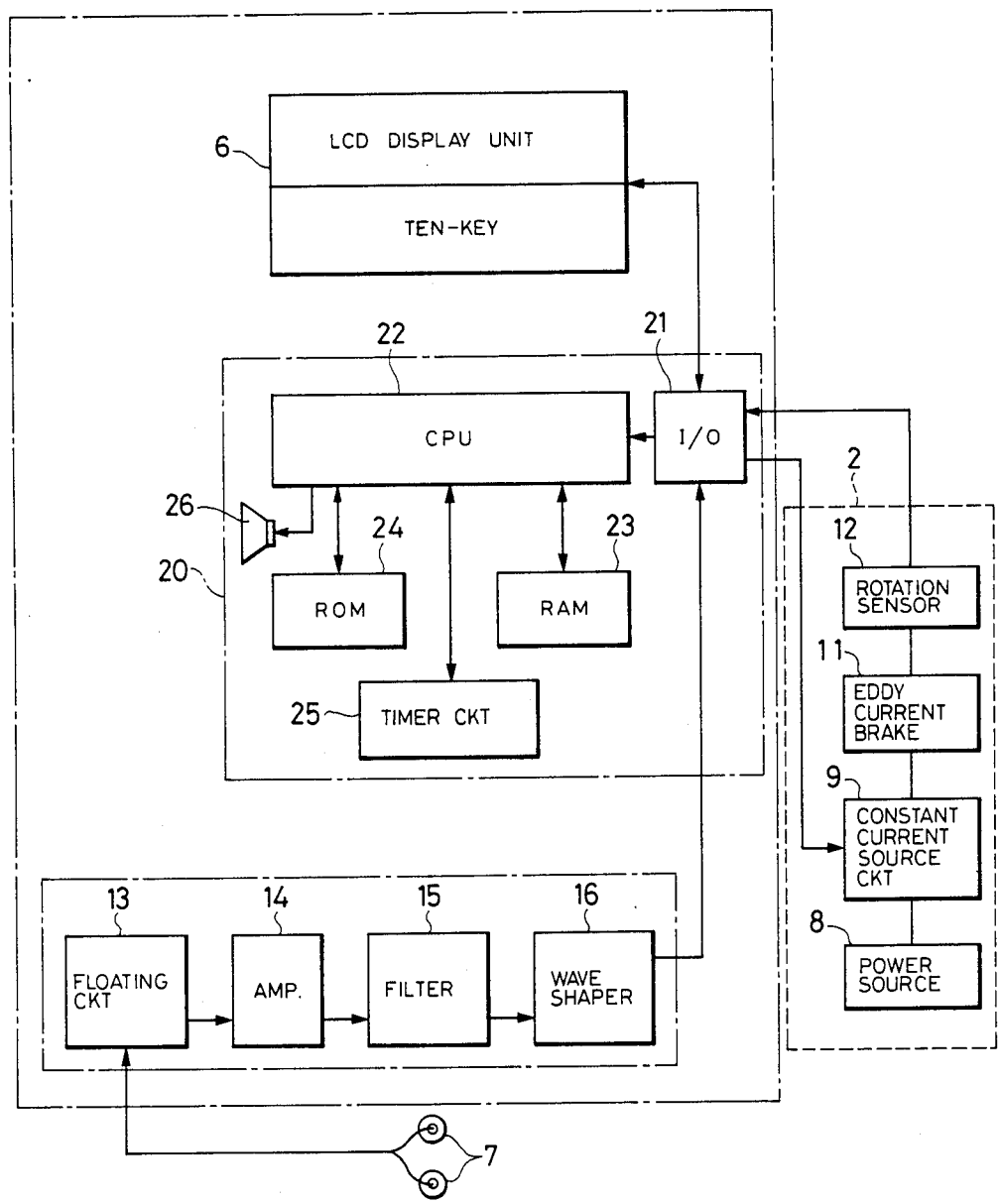
FIG. 2 is a block diagram of a control section in the training device shown in FIG. 1.

In FIG. 1 is shown a training device 10 of the invention, namely, a bicycle ergometer which loads the operator with his flexing motion. The training device 10 includes a frame 1 and loading means 2 rotatably supported by the frame 1. The loading means 2 is made up of, for instance, an eddy current brake, only the essential part of which is shown in FIG. 1. The eddy current brake has been described in Japanese Patent application No. 123171/1983 by the present applicant. Pedals 3 powered by the user rotate the loading means 2. A saddle 4 is mounted on a supporting member extended from the frame 1 in such a manner that the saddle 4 is movable vertically. In front of the saddle 4, there is provided a handle bar 5 which is fixedly mounted on a supporting member extended from the frame 1. An input/output box 6 is mounted in the middle of the handle 5. The input/output box 6 is used to input physical conditions (described later) and to output and display predetermined data. Electro-cardio-potential sensors 7 (each comprising a conductive rubber electrode or an Ag/AgCl disposal electrode) are connected to one side of the input/output box 6. Installed inside the frame 1 are the aforementioned loading means 2 and, as shown in FIG. 2, a power source 8 for supplying current and voltage to various parts of the bicycle ergometer and various other circuits shown in FIG. 2. These other circuits include a constant current control circuit 9, an eddy current brake 11, a rotation sensor 12, a floating circuit 13, an amplifier 14, a filter 15, an electro-cardio-potential waveform shaping circuit 16 and a microcomputer 20 (described later).

FIG. 2 shows the means for controlling the training device for rehabilitation according to the invention, i.e., the bicycle ergometer 10. The controlling means comprises the aforementioned input/output box 6, an arithmetic and control unit arranged near the loading means 2, and a peripheral unit related thereto. The microcomputer 20 includes an input/output unit (hereinafter referred to as "an I/O unit 21"), a central processing unit (CPU) 22, a random access memory (RAM) 23, a read-only memory (ROM) 24, a timer circuit 25 and a buzzer 26.

The microcomputer 20 operates to read processing programs for rehabilitation out of the ROM 24. The microcomputer 20 also, according to the processing program thus read, inputs to the CPU 22 through the I/O unit 21, according to the processing program thus read, both data supplied from the input/output box 6 such as physical conditions (for instance a target heart rate specified by the doctor after a heart disease has been cured), as well as signals from the electro-cardio-potential sensors 7 and the rotation sensor 12. The microcomputer 20 further operates to store in the RAM 23 various data processed by the CPU 22, to transfer the processing program for rehabilitation read out of the ROM 24 to the RAM 23, and to control the amount of load of the loading means 2 through the constant current control circuit 9 according to the processing program thus transferred. Then, according to the data finally provided by RAM 23, the CPU 22 operates to apply predetermined data such as a desired heart rate and a load value through the I/O unit 21 to the input/output box 6 so that the data are displayed.

Figure 3:
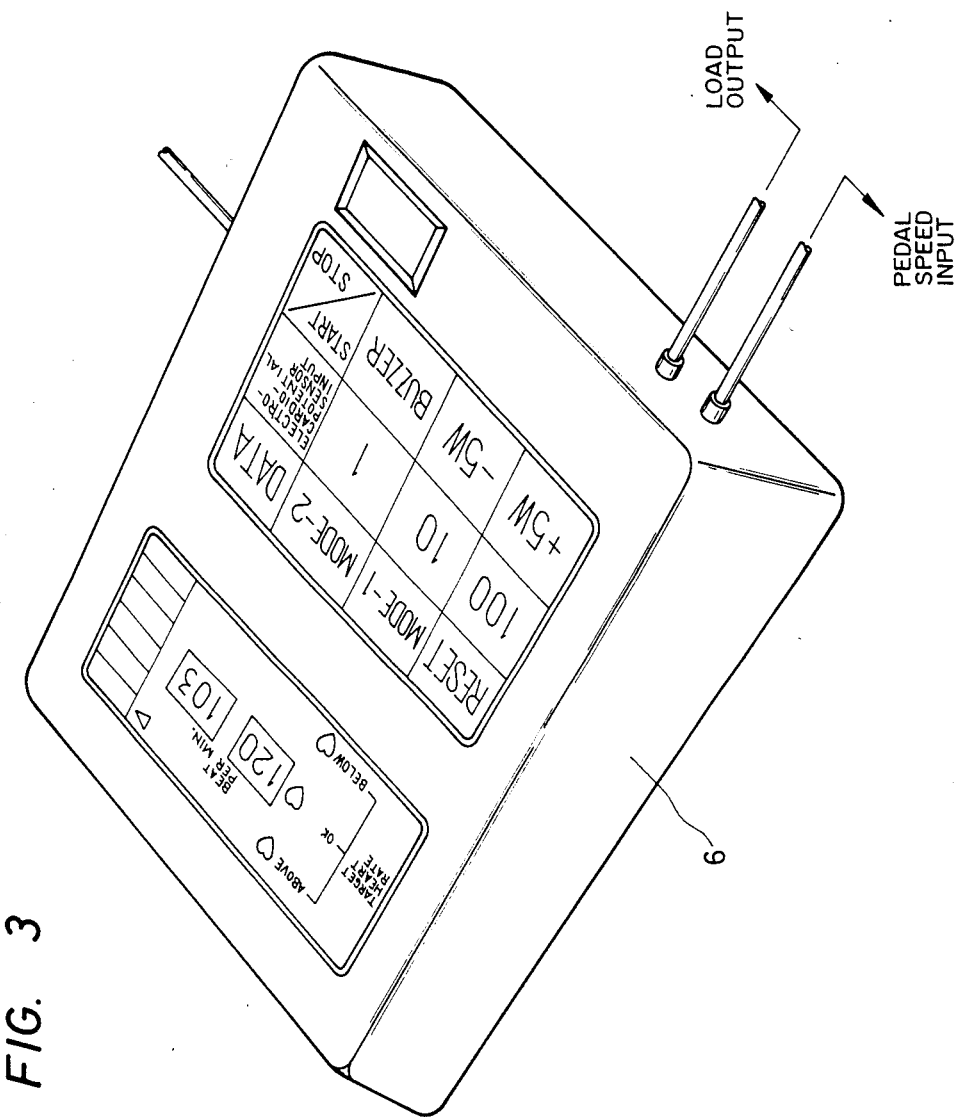
FIG. 3 is a perspective view of a control box in the training device.

FIG. 3 shows the front panel of the input/output box 6. A display section is provided in the upper portion of the front panel for displaying the target heart rate, a range of the variable numbers of heart rates, time, a load value, a calorie value, a distance and the revolutions. Various keys for inputting various data required for rehabilitation such as physical conditions (age, sex, etc.) are provided in the lower portion of the front panel.

Figure 4A:
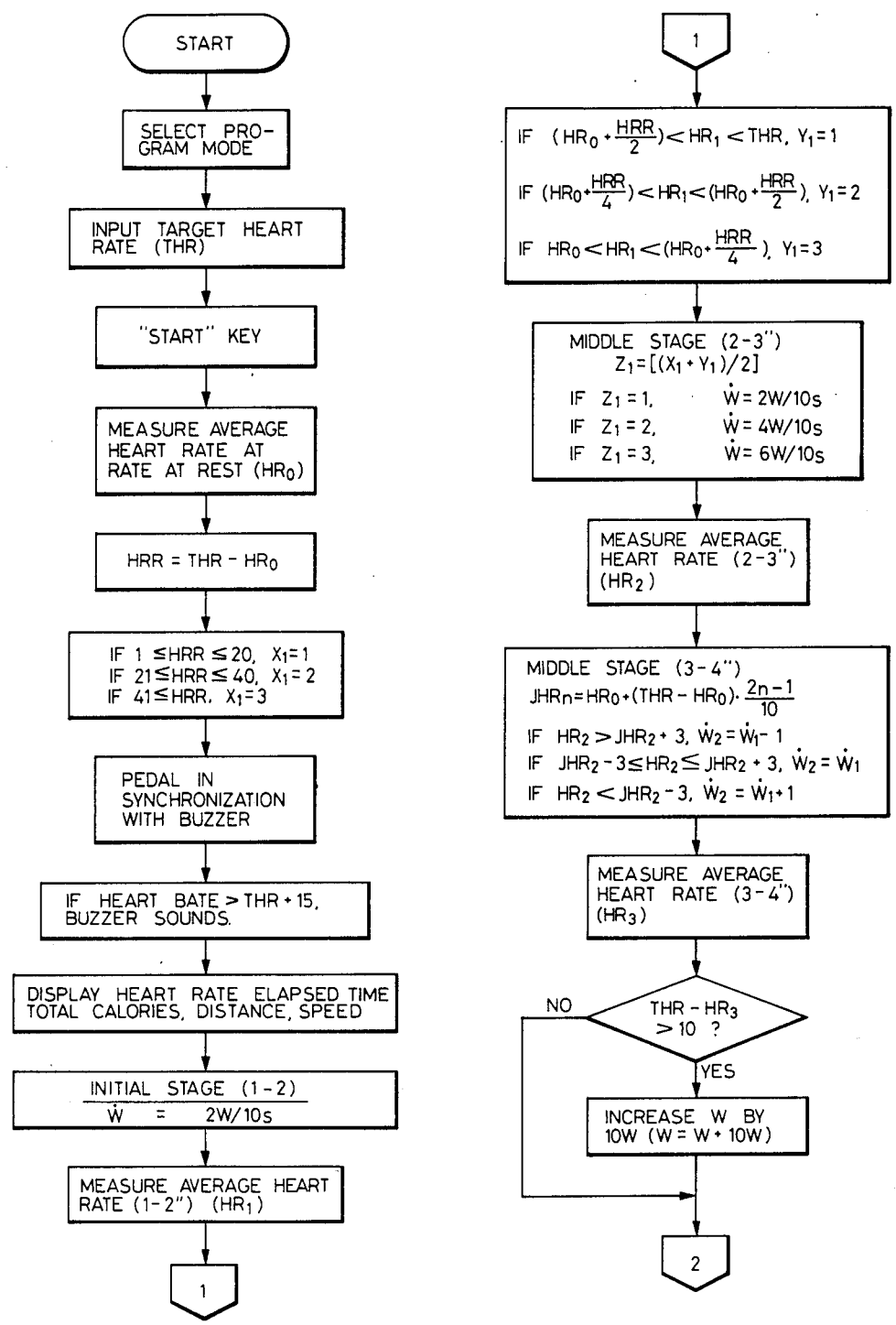
FIGS. 4a and 4b are two parts of a flow chart for a description of the operation of the training device for rehabilitation according to the invention.

Now, a rehabilitation exercise carried out with the bicycle ergometer 1 thus constructed will be described with reference to FIGS. 4a, 4b and 5.

First, the operator (or user) sits on the saddle 4 of the bicycle ergometer 1 shown in FIG. 1 and selects a desired program mode by operating the corresponding key on the front panel of the input/output box 6 shown in FIG. 3. The user then fixes the electro-cardio-potential sensors 7 on the right and left of his chest (with the reset key depressed). Thereafter, he inputs the target heart rate (THR) specified by the doctor. Now, he can start the rehabilitation by depressing the start key.

When the rehabilitation exercise is started in this manner, the desired program is read out of the ROM 24. At the same time, the timer circuit 25 coupled to the CPU 22 starts its operation, so that pulses from the sensors 7 (with the operator at rest) are measured for about one minute (the current heart rate being sampled n times each for m seconds for a correct value). The average heart rate per minute with an operator at rest $HR_o$ (hereinafter referred to as "the average heart rate at rest $HR_o$") is obtained by averaging the heart rates thus measured. Then the heart rate reserve HRR is obtained by subtracting the heart rate at rest $HR_o$ from the target heart rate THR ($HRR = THR - HR_o$). The heart rate reserve is utilized to determine a value for $X_1$ of 1, 2 or 3 according to the program, where a large value of $X_1$ corresponds to a large heart rate reserve.

Figure 5:
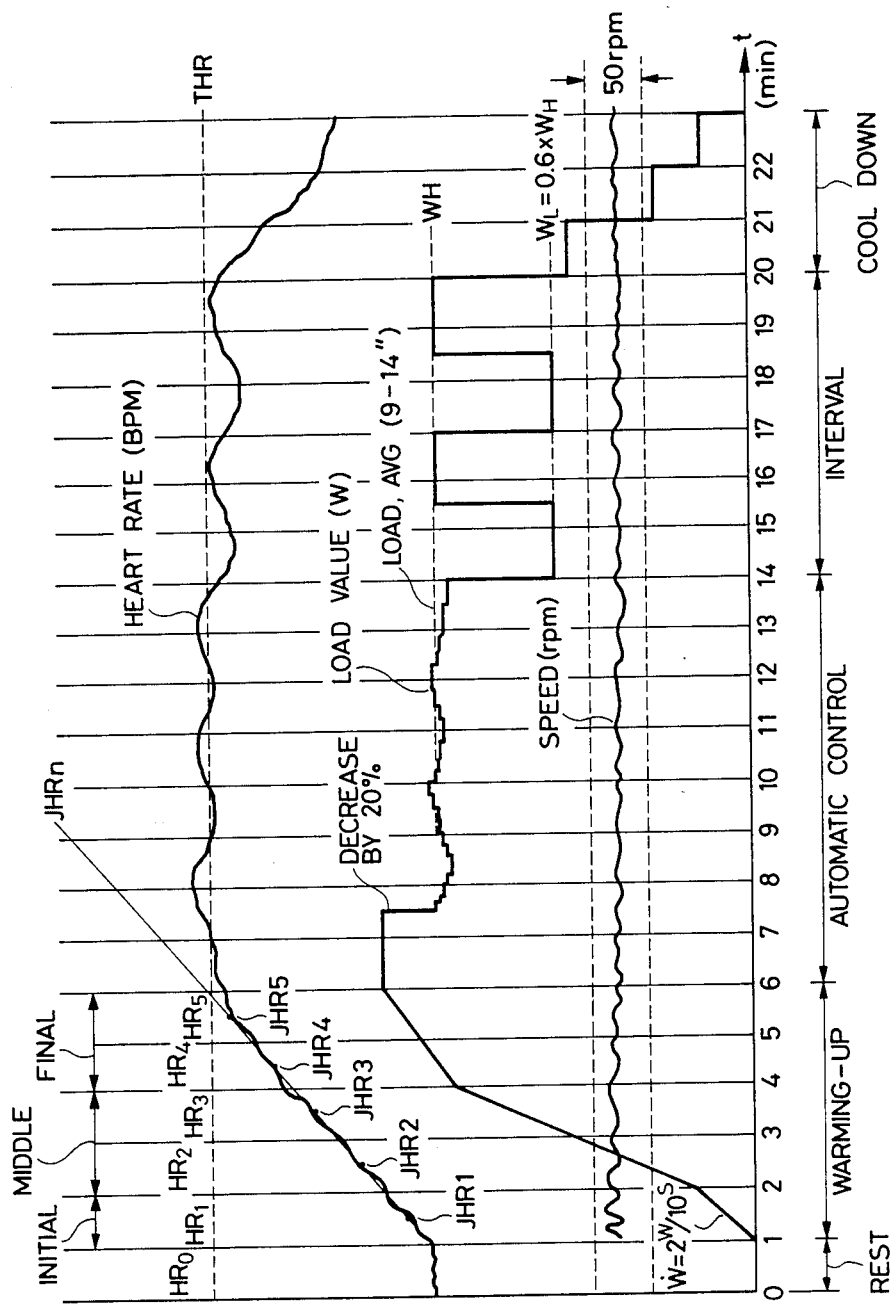
FIG. 5 is a time chart showing training program data in the training device according to the invention.

After the measurement of the average heart rate at rest $HR_o$ and the heart rate reserve HRR have been determined, the operator pedals in synchronization with sounds produced at equal intervals; that is, the initial warming-up operation of FIG. 5 is effected. In this case, when the heart rate of the operator exceeds the preset sum of the target heart rate THR plus fifteen (THR+15), the buzzer 26 operates, thus warning him that he should stop the exercise. The increment of +15 is the numerical value for adjusting the sensitivity of the buzzer. For a rehabilitation exercise, the numerical value of the increment is preferably set to about +5 thereby to increase the sensitivity of the buzzer because the user can exercise himself while feeling at rest. That is, the warming-up can be continued until the buzzer 26 operates.

In the warming-up period, the load value W of the load means 2 is controlled with a moderate rise of $dw/dt = \Delta W/\Delta t$, for instance 2w/10 sec, i.e. 0.2 watts/sec, because of the initial warming-up. Further in the initial warming-up, the average heart rate $HR_1$ per minute is obtained similarly as in the case of the above-described average heart rate at rest $HR_o$ and a value $Y_1$ of 1, 2 or 3 shown in the flow chart of FIG. 4a is determined. That is, the value $Y_o$ is determined according to where the average heart rate $HR_1$ is located between the heart rate at rest $HR_o$ and the target heart rate THR, with a large value of $Y_1$ corresponding to a low heart rate.

After the warming-up period of one minute has passed, the middle warming-up operation is effected for about two to four minutes. In the middle warming-up operation, the loading means 2 is controlled according to a load value which is determined by a value $Z_1$ where $Z_1 = (X_1 + Y_1)/2$ with any non-integer part disregarded, as shown in the flow chart of FIG. 4a. In the middle warming-up stage, because of the middle warming-up, the load rise rate is larger than that in the initial warming-up stage. Specifically, $\Delta W/\Delta t = 2w/10$ sec when $Z_1 = 1$, $\Delta W/\Delta t = 4$ w/10 sec when $Z_1 = 2$, and $\Delta W/\Delta t = 6$ w/10 sec when $Z_1 = 3$.

In the middle warming-up stage also, the average heart rate $HR_2$ is measured for the third (2-3) minute. The value W is suitably corrected by utilizing the average heart rate $HR_2$ and a value $JHR_n$ where $JHR_n = HR_o + (THR - HR_o) \times (2n-1)/10$ and n=1 to 5. For instance, $W_2 = (W_1 - 1)$ when $HR_2 > JHR_2 + 3$, $W_2 = (W_1 + 0)$ when $JHR_2 - 3 \leq HR_2 \leq JHR_2 + 3$, and $W_2 = (W_1 + 1)$ when $HR_2 < JHR_2 - 3$.

The above-described control of the loading means 2 is carried out also for the fourth (3-4) minute. The average heart rate $HR_3$ is measured for the fourth minute. Then, it is determined whether or not the difference between the average heart rate $HR_3$ and the target heart rate THR is larger than ten (10) heart beats. If the difference $(THR - HR_3)$ is larger than ten (10), then the load value is increased by 10 w, and if smaller, he may continue the middle warming-up.

In the above-described embodiment, the difference between the average heart rate $HR_3$ and the target heart rate THR is compared with ten (heart beats) to determined whether or not the load should be increased by 10 w. However, the reference value may be smaller than ten, and the increment W is not limited only to 10 w.

The third-and-fourth-minute middle warming up stage is followed by the final warming-up stage which lasts for another two minutes (the fifth and sixth minutes).

Figure 4B:
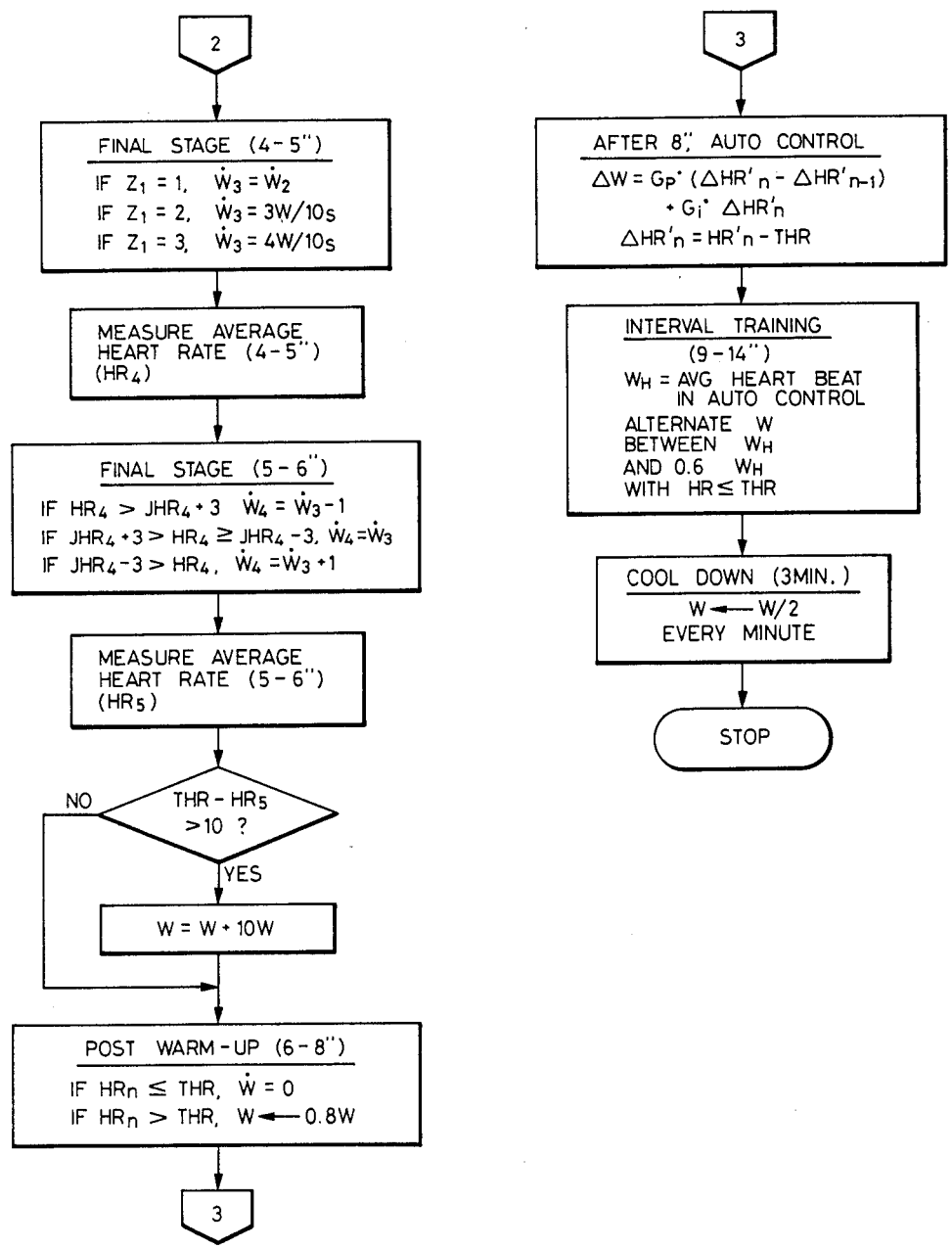

In the final warming-up stage, the loading means 2 is controlled according to a load value W which is determined by the value $Z_1$ shown in the flow chart of FIG. 4b. In the final warming-up stage, because of the final warming-up the load rise rate is smaller than that in the middle warming-up stage; $\Delta W_3/\Delta t = \Delta W_2/\Delta t$ when $Z_1 = 1, \Delta W_3/\Delta t = 3w/10$ sec when $Z_1 = 2$, and $\Delta W_3/\Delta t = 4$ w/10 sec when $Z_1 = 3$. In the final warming-up stage also, the average heart rate $HR_4$ is measured for the fifth (4-5) minute. The average heart rate $HR_4$ and a value $JHR_4$ are utilized to suitably correct the value W. Namely $\Delta W_4/\Delta t = (\Delta W_4/\Delta t - 1)$ when $HR_4 > JHR_4 + 3$, $\Delta W_4/\Delta t = (\Delta W_3/\Delta t + 0)$ when $JHR_4 - 3 \leq HR_4 \leq JHR_4 + 3$, and $\Delta W_4 - \Delta t \times (\Delta W_3/\Delta t + 1)$ when $HR_4 < JHR_4 - 3$.

The control of the loading means 2 is carried out in the same manner for the sixth (5-6) minute. In the sixth minute also, the average heart rate $HR_5$ is measured. Then, it is determined whether or not the difference between the target heart rate THR and the average heart rate $HR_5$ (THR $- HR_5$) is larger than ten (10) heart rate. If the difference is larger than ten (10), then the load value W is further increased by 10 watts, and if smaller, the operator may continue the final warming-up.

In the above-described embodiment, the difference between the average heart rate $HR_5$ and the target heart rate THR is compared with ten (heart beats) to determine whether or not the load should be increased by 10 w. However, the reference value may be smaller than ten, and the increment to W is not limited only to 10 w.

Thus, the loading means 2 has been so controlled by the five-minutes warming up that it is most suitable to the user.

If, even after the warming-up, the heart rate does reach the target heart rate THR, the load value W is maintained as it is. When the heart rate exceeds the target heart rate THR, the load value is decreased by about 20%. The decrease of the load value depends on the physical conditions and strength of the person being rehabilitated. However it has been found through past experimental rehabilitations that, if, after the warming-up, the load means 2 is controlled with the load value determined in the final warming-up stage, the heart rate of the operator greatly exceeds the target heart rate THR. Therefore, the decrease of the load value is so programmed that it is carried out within about two minutes after the warming-up. According, in the embodiment, with the load value W decreased by about 20%, an automatic control is carried out after the eighth minute. That is, a rehabilitation exercise is conducted for about six minutes with the heart rate being maintained equal to the target heart rate THR.

In the automatic control, the load is determined by the following expression:

$$\Delta W = G_p(\Delta HR_n' - \Delta HR_{n-1}') + G_i \Delta HR_n' \qquad (W)$$

where $\Delta W$ is the amount of adjustment of the load W, $HR_n'$ is the heart rate at the time instant $t_n$, $\Delta HR_n' = HR_n' - THR$ so that $\Delta HR_n'$ is the deviation, $G_p$ is a proportional constant, THR is the target heart rate, $G_i$ is an integral constant, and $t_s = t_n - t_{n-1}$ is the $HR_n$ sampling period. In the preferred embodiment $G_p = 1$, $G_i = 1$, and $t_s = 20$ sec. However, these values may be changed.

The automatic control rehabilitation training period described above is followed by an interval training period. For the interval training period, an average load value $W_H$ is determined for the last five minutes of the automatic control rehabilitation training period and is used as an upper reference value. A lower reference is value $W_L$ is determined as $W_L = W_H \times 0.6$. The two reference load values $W_H$ and $W_L$ are alternately and repeatedly given for the load value W to the extent that the heart rate does not exceed the target heart rate THR. The average load value $W_H$ can either be measured or, more easily, be calculated from previously set values of the load W over the period of 9" to 14".

This interval training period is the most specific feature of the invention. As was described before, immediately after the heart disease has been cured, the patient's physical condition is much lower than that of a healthy person. Therefore, a warming-up exercise is suitably conducted before the rehabilitation training, the rise of the heart rate and the increase in fatigue of the muscles of the legs and the waist are liable to be unbalanced with each other. Accordingly, even in the case where it seems that the heart rate of the operator is much different from the target heart rate, the muscles of the feet and the waist are often greatly fatigued. Under this condition, continuation of the above-described automatic control training is not suitable for the rehabilitation, and may sometimes be considerably dangerous for him.

In order to eliminate the above-described difficulties, in the invention, the interval training period is provided in the training program, so that the rehabilitation training is effectively and safely carried out with good balance kept between the rise of the heart rate and the increase in fatigue of the muscles of the legs and the waist.

In the above-described embodiment, the upper interval load value $W_H$ is multiplied by a factor of 0.6 to obtain the lower interval load value $W_L$. However, the factor may be changed according to the physical condition of the operator in forming the training program.

The above-described interval training period is followed by a cool-down period (three minutes). The cool-down period is so programmed that the load value is decreased by half every minute and finally set to zero.

Thus, one cycle of rehabilitation training has been accomplished.

As was described above, in the training device for rehabilitation according to the invention, the load control means is provided to allow the heart rate to smoothly reach the target value at a predetermined rate in the warming-up exercise. After the target value has been reached, the load is controlled so that the target value is maintained within the predetermined range. The load value for a predetermined period is measured, and the interval training period is included in which the load is alternately increased and decreased according to the load value thus measured. Furthermore the load control means is provided so that, before the training is ended, the cool-down period is provided to gradually decrease the load value. The load value is so controlled that the heart rate measured is compared with that measured earlier so that the difference therebetween is corrected. Therefore the training device for rehabilitation according to the invention is considerably effective in rehabilitating the person who is attempting to regain his health after heart disease.

As was described above, the rehabilitation training program is the invention has at least four training steps; warming up, automatic control, interval, and cool-down. The physical data of the operator at rest before the warming-up and those measured several times during the warming-up period are processed by the predetermined processing means so that the load control range is determined for each of the aforementioned steps. The load is increased or decreased according to the variation of the physical data of the operator which are measured during his continuous training so that the physical conditions of the operator conform to the above-described range. Therefore in the invention, after the operator is held at rest, a relatively long warming-up period is provided so that the heart rate of the operator is increased substantially linearly towards the target value during the warming-up period. In the automatic control step, the heart rate set for the rehabilitation of the operator is maintained substantially constant and the average load value required for maintaining that heart rate is measured. The average load value thus measured is utilized in the following interval step so that, while the target heart rate is maintained optionally, the load is intermittently decreased to thereby decrease the load applied to the legs and waist. Therefore, the physical power of a person who has recovered, for instance, from heart disease can be increased with the training device of the invention. Furthermore, the training device of the invention is so designed that the target heart rate is inputted according to the doctor's instruction for the person who has recovered from the heart disease. Therefore, the rehabilitation can be readily conducted at places other than rehabilitation centers.

What is claimed is:

1. A rehabilitation training device in which at least four training steps of warming-up, automatic control, interval control and cool-down are provided, said rehabilitation training device comprising:
   pulse rate measuring means for detecting a heart rate of a user at rest before said training steps and during said training steps;
   data inputting means for freely setting a target heart rate as an exercise reference for said user;
   processing circuit means for processing input data from said pulse rate measuring means and said data inputting means;
   an ergometer for being operatively manipulated by a said user and having a load controlled by an output of said processing circuit means;
   warm-up control means for gradually increasing said load of said ergometer during said warm-up step until a detected heart rate of said user reaches said target heart rate;
   automatic control means for controlling said load of said ergometer during said automatic control step so that, after reaching said target heart rate, a detected heart rate is maintained within a predetermined tolerance of said target heart rate;
   interval control means for changing said load of said ergometer during said interval control step at intervals, according to an average load value of said load during a predetermined period of said automatic control step; and
   cool-down control means for gradually decreasing said load of said ergometer during said cool-down step following said interval control step; and
   wherein said warm-up control means, said automatic control means, said interval control means and said cool-down control means being provided in conjunction with an operation of said processing circuit.

2. A rehabilitation training device as recited in claim 1, wherein said processing circuit determines a load control setting range for each of said steps, and increases or decreases said load of said ergometer dependent upon pulse rate input data from said heart rate measuring means, so that a detected heart rate is maintained using said load control setting range.

3. A rehabilitation training device as recited in claim 2, wherein said interval control means alternately changes said load between said average load value and a predetermined fraction of said average load value.

4. A method for controlling a rehabilitation training device which includes an ergometer having variable load means, pedal means to be operatively manipulated by a user, and a sensor for measuring heart beats of said user, said method comprising the steps of:

inputting a target heart rate as an exercise reference for said user;

measuring a heart rate of said user while at rest, and while training on said ergometer;

processing said target heart rate and a heart rate from said measuring step to produce a load value for said ergometer; and setting a load on said ergometer to said load value;

wherein said processing step including the sub-steps of:

gradually increasing said load value during a warm-up period until a measured heart rate reaches said target heart rate;

controlling said load value during an automatic control period so that after reaching said target value, a measured heart rate is maintained within a predetermined tolerance of said target heart rate;

changing said load value at intervals during an interval training period, said changing step being conducted according to an average value of said load value during said controlling step; and gradually decreasing said load value in a cool-down period following said changing step.

* * * * *